(12) United States Patent
Skene et al.

(10) Patent No.: US 8,028,706 B2
(45) Date of Patent: Oct. 4, 2011

(54) METHOD FOR CONTROLLING THE ALERTNESS OF A HUMAN SUBJECT AND A LIGHT SOURCE FOR USE IN THIS METHOD

(75) Inventors: Debra J. Skene, Guildford (GB); Josephine Arendt, Guildford (GB); Kavita Thapan, Guildford (GB); Gerrit Jan Van Den Beld, Eindhoven (NL); Petrus Johannes Mathijs Van Der Burgt, Eindhoven (NL)

(73) Assignee: Koninklijke Philips Electronics N. V., Eindhoven (NL)

( * ) Notice: Subject to any disclaimer, the term of this patent is extended or adjusted under 35 U.S.C. 154(b) by 1623 days.

(21) Appl. No.: 10/129,696

(22) PCT Filed: Sep. 7, 2001

(86) PCT No.: PCT/EP01/10677
§ 371 (c)(1),
(2), (4) Date: Sep. 16, 2002

(87) PCT Pub. No.: WO02/20079
PCT Pub. Date: Mar. 14, 2002

(65) Prior Publication Data
US 2003/0069616 A1    Apr. 10, 2003

(30) Foreign Application Priority Data

Sep. 8, 2000   (GB) .................................. 0022089.7
Sep. 13, 2000  (EP) .................................. 00203180
Oct. 13, 2000  (GB) .................................. 0025207.2

(51) Int. Cl.
*A61B 19/00* (2006.01)
(52) U.S. Cl. ........................................ 128/898; 607/88

(58) Field of Classification Search .............. 607/88–91; 128/898
See application file for complete search history.

(56) References Cited

U.S. PATENT DOCUMENTS

| 4,444,190 | A |   | 4/1984  | Mutzhas              |
|-----------|---|---|---------|----------------------|
| 5,083,858 | A |   | 1/1992  | Girerd ............. 351/44 |
| 5,163,426 | A |   | 11/1992 | Czeisler et al.      |
| 5,167,228 | A |   | 12/1992 | Czeisler et al.      |
| 5,176,133 | A | * | 1/1993  | Czeisler et al. ...... 607/88 |

(Continued)

FOREIGN PATENT DOCUMENTS

DE          19549092 A1    8/1997

(Continued)

OTHER PUBLICATIONS

G.C. Brainard et al; "Effect of Light Wavelength on the Suppression of Nocturnal Plasma Melatonin in Normal Volunteers", Annals of New York Academy of Sciences 453, (1985), p. 376-378.

(Continued)

*Primary Examiner* — Ahmed M Farah

(57) ABSTRACT

The invention relates to a method for controlling the alertness of a human subject and a light source for use in this method and use of a light source for this method. The method comprises exposure of a human subject during an exposure period to suitable light radiation without substantially influencing the phase of a melatonin cycle. Melatonin is a sleep-hormone that can be used to control the alertness of a human subject. The suitable light radiation being specified by an output fraction of melatonin suppressive radiation (Melatonin Watt/Watt) and light output (lumen/Watt), the output fraction and light output being adjusted to obtain the desired effect on the phase of said cycle.

11 Claims, 5 Drawing Sheets

U.S. PATENT DOCUMENTS

| | | | | |
|---|---|---|---|---|
| 5,197,941 | A | * | 3/1993 | Whitaker .................. 600/27 |
| 5,292,345 | A | | 3/1994 | Gerardo |
| 5,304,212 | A | | 4/1994 | Czeisler et al. ............ 607/88 |
| 5,447,528 | A | | 9/1995 | Gerardo ..................... 607/88 |
| 5,503,637 | A | | 4/1996 | Kyricos et al. .............. 607/88 |
| 5,545,192 | A | * | 8/1996 | Czeisler et al. ............ 607/88 |
| 5,562,719 | A | * | 10/1996 | Lopez-Claros ............ 607/88 |
| 5,589,741 | A | * | 12/1996 | Terman et al. ............ 315/360 |
| 5,805,267 | A | | 9/1998 | Goldman |
| 5,919,217 | A | | 7/1999 | Hughes ..................... 607/90 |
| 5,923,398 | A | * | 7/1999 | Goldman ................... 351/203 |
| 6,135,117 | A | * | 10/2000 | Campbell et al. .......... 128/898 |
| 6,235,046 | B1 | * | 5/2001 | Gerdt ........................ 607/88 |
| 7,438,418 | B2 | | 10/2008 | Marshall |
| 7,678,140 | B2 | | 3/2010 | Brainard et al. |
| 2003/0069616 | A1 | | 4/2003 | Skene et al. |

FOREIGN PATENT DOCUMENTS

| | | |
|---|---|---|
| EP | 0363440 B1 | 5/1997 |
| EP | 0477282 B1 | 5/1997 |
| WO | 9851372 A1 | 11/1998 |
| WO | 0002491 A1 | 1/2000 |
| WO | 0185254 A1 | 11/2001 |
| WO | 03105185 A1 | 12/2003 |
| WO | 2004088616 A1 | 10/2004 |

OTHER PUBLICATIONS

Baker, Use of a circadian lighting system to improve night shift alertness and performance at the USNRC's headquarters operations center', Safety of Operating Reactors Proceedings, Sep. 1995, pp. 811-818.

Brainard et al., "Effect of light wavelength on the suppression of nocturnal plasma melatonin in normal volunteers", 1985, pp. 376-378.

Colquhoun et al, "Shiftwork: Problems and solutions", 1996, pp. 113-139, Germany.

Brainard et al, "Ocular mechanisms that regulate the human pineal gland", Advances in Pineal Research: Aug. 1994, pp. 415-432, John Libbey & Company Ltd.

LRC, "Evaluating interior lighting schemes", Rensselaer, Sep. 2000.

Morita et al., "Effects of lights of different color temperature on nocturnal changes in core temperature and melatonin in humans", Applied Human Science: Journal of Physical Anthropology, 1996, pp. 243-246, Japan.

* cited by examiner

METHOD FOR CONTROLLING THE ALERTNESS OF A HUMAN SUBJECT AND A LIGHT SOURCE FOR USE IN THIS METHOD

The invention relates to a method for controlling the alertness of a human subject via suitable light radiation.

The invention further relates to a method of adjustment of the circadian pacemaker and to a light source for use in these methods.

In the last decade the knowledge of human photobiology is increased tremendously and has made clear that light radiation that is administered to the human subject through the eye—in addition to vision—is of major importance in controlling a variety of biological rhythms. Consequently light radiation has influence not only on many physical body functions but also on mental performance and mood. All scientific evidence is for the major part based on administering 'white light radiation' of various intensities to the eye, this is generally known and for example described in U.S. Pat. No. 5,545,192. Findings show a sensitivity of melatonin suppression for light radiation administered through the eye, the melatonin suppression being dependent on dose and spectral composition of the light radiation, see Annals New York Academy of Sciences 453 (1985), p.376-378. Melatonin is a hormone which shows a daily cycle and is considered as a marker of the phase of the biological rhythms. Melatonin is generally known as a sleeping hormone that influences the alertness of the human subject. Hence, when the melatonin cycle is controlled, the risk on making mistakes because of lack of alertness is decreased. A relatively low melatonin level stimulates alertness, a relatively high melatonin level increases sleepiness. Annals New York Academy of Sciences 453 (1985), p.376-378, states that the suppression of melatonin shows a highest sensitivity at a wavelength of about 509 nm. Suppressing melatonin is in the natural daily cycle possible in the 'dark' hours, so where there is only artificial illumination available. During daytime the melatonin level is relatively low, the level increases in the evening, and reaches a maximum at night and decreases gradually to the level during daytime, in the wake up period. In a 24-hour society many people have to work and drive at night and be alert to perform well and safe, and to sleep well at abnormal hours. Under these conditions many people run an enhanced risk on making mistakes, for example causing car accidents, and/or are likely to suffer from a distorted sleeping behavior.

It is an object of the invention to provide a method via which the risk on making mistakes of people that have to function at abnormal hours during the day is reduced.

According to the invention, this object is achieved via a method for controlling the alertness of a human subject via suitable light radiation, the human subject having a cycle of melatonin variation involving at least phases of a melatonin built-up and a melatonin degradation and being in a phase of said cycle, by suppressing or allowing said melatonin built-up or by stimulating said melatonin degradation, the method comprising the step of:

exposing the human subject during an exposure period to the suitable light radiation in dependence of a desired effect on the phase of said cycle, said desired effect being the suppression of said melatonin built-up or being the stimulation of said melatonin degradation or being illumination of the human subject without substantially influencing the phase of said cycle, optionally while screening of ambient light radiation and optionally with interval periods without said suitable light radiation in-between two exposure periods, wherein the suitable light radiation is specified by an output fraction of melatonin suppressive radiation (Melatonin Watt/Watt) and light output (lumen/Watt), the output fraction and light output being adjusted to obtain the desired effect on the phase of said cycle.

Recent findings deviate from earlier statements that the sensitivity of melatonin suppression would be similar to scotopic night-vision sensitivity, as the maximum sensitivity for scotopic vision is at a wavelength of about 509 nm. Surprisingly, it appeared that the melatonin suppression sensitivity, compared with the scotopic night vision sensitivity, is shifted towards a shorter wavelength region. It is particularly surprising that short wavelengths should have such a substantial effect on the melatonin suppression as the vast majority of recognized light receptors in the retina have activation wavelengths of 500 nm or greater. Below 500 nm, the only recognized receptors are the blue cones, which have $\lambda_{max}$ of 420 nm, and these are present in amounts corresponding to less than 1% of any other family of light receptors in the retina.

It is particularly advantageous that such short wavelength light is able to suppress melatonin production as considerably less light is required, owing to its increased efficacy. In addition, the amount of light that is necessary to effect melatonin suppression can be substantially reduced if the optimal wavelength, or band of wavelengths, is selected, thereby avoiding any problems with sight caused by undue glare or intense illumination.

Melatonin is produced by the pineal gland, and it is believed that appropriate afferent optical nerves have an effect on the production of melatonin by the pineal gland. In particular, it is demonstrated that subjects directly observing a source of short wavelength light experience an acute reduction in the production of melatonin. However, there is also evidence that administration of light to non-ocular parts of the body can also affect the melatonin suppression of the subject. Accordingly, it is preferred that the light of the present invention is administered ocularly, but it will be appreciated that administration to other parts of the body is also envisaged. Besides, the doses to suppress melatonin as function of the wavelength are known for fully dilated pupils.

The experiments demonstrate that the greatest sensitivity to short wavelength light is in the region just above the ultraviolet. Ultraviolet is generally accepted as being light radiation below about 380 nm. In particular, we have shown that there is particularly high sensitivity to light in the region of 420-460 nm, and this sensitivity tails off with higher wavelengths, with decreasing efficacy to about zero at 560 nm. As noted above, the wavelength of the light is greater than ultraviolet, although the present invention envisages wavelengths in the broader region with ultraviolet. In general, though, ultraviolet light should be avoided, in order to minimize risk to the subject. Administering melatonin suppressive radiation can be integrated in light sources for vision, or in separate additional 'light' sources, or also in other light generating objects, for example integrated in monitors, TV sets, reading or even breakfast tables, goggles, visors, artificial windows. Many applications of light radiation for effective melatonin suppression or melatonin maintenance are detected in the home environment, the working place and in traffic and transportation. On basis of the present data several basic options for spectral distributions of the light radiation are distinguished:

Melatonin suppressive radiation and sufficient visible light for correct task performance, for example an accepted standard light level is a light level of at least 200 lux (lux means lumen/m$^2$). Applications are found for example in the shift work activities, including morning, evening and night shifts both indoor and outdoor.

Melatonin suppressive radiation and dim visible light level, i.e. about 10 lux, or less. For comparison, full moon light means a visible light level of less than 1 lux. Options are in evening and night for example for drivers, surveillance, guards, and nurses.

Melatonin maintaining radiation and sufficient visible light for correct task performance. Major applications are expected for example in evening work and providing the conditions for good quality sleep afterwards for elderly people at home.

An estimation of the effectiveness of spectral power distributions of the radiation for melatonin suppression and luminous flux is obtainable via calculations. In the calculations only the spectral power is considered between wavelengths 380-740 nm. All spectra are normalised in such way that the sum of the spectral power in the range 380-740 nm is equal to one watt. In formula:

$$\Sigma E(\lambda)=1 \text{ Watt}$$

wherein λ=380-740 nm.

To calculate the luminous flux and the melatonin effective Watts (melatonin Watts) the following formulas have been used:

$$\text{Luminous flux} \Phi=683*\Sigma(E(\lambda)*V(\lambda))$$

$$\text{Melatonin Watts}:=\Sigma(E(\lambda)*M(\lambda)).$$

In which:
V(λ) is the eye sensitivity flux;
M (λ) is the melatonin sensitivity;

The constant value of 683 is the luminous flux obtained by 1 Watt of light having a wavelength of 555 nm, being the maximum of the eye sensitivity.

FIG. 4 shows a typical melatonin sensitivity curve for people in the age of 20-40 years as obtained from experimental results. As the melatonin sensitivity is a.o. dependent on the transmission of the lens of the eye, which on its turn is dependent on the age of the human subject, the efficiency of melatonin suppression via light radiation generally decreases by increasing age of the human subject. The melatonin effective Watts can then be calculated according to $$\text{Melatonin Watts } M_{age}(\lambda):=\Sigma(E(\lambda)*M(\lambda)*T(\lambda)),$$

wherein T(λ) is the fraction of lens transmission.

FIG. 4 shows a typical example of a melatonin sensitivity curve for elderly people (>=60 years) corrected for the lens transmission.

In an embodiment, the method is characterized in that the output fraction of melatonin suppressive radiation is>=0.45 Melatonin Watt/Watt and the light output is<=60 lumen/Watt. Via this method the melatonin is suppressed efficiently but with relatively low output of visible light radiation. These methods are particularly suited for nursing activities. However, as the eye sensitivity for light is dependent on the age of the human, an embodiment is preferred in which the method is characterized in that the output fraction of melatonin suppressive radiation is>=0.45 Melatonin Watt/Watt and that the light output is <=20 lumen/Watt. This method is particularly appropriate to be used for relatively young people who have a high sensitivity for light, the melatonin is suppressed efficiently and the output of the visible light radiation is very low. As the melatonin suppression is obtainable by light radiation that yield only a very low amount of visual light/lumen, i.e. deep blue, the melatonin suppressive radiation hardly influences the visual conditions created by light for vision purposes. These methods find their application in activities in which a dim visible lighting level is needed but in which activities require that people has to be kept alert and awake, for example in control rooms of an air field. Yet, even more demands are posed upon lighting levels for truck drivers at night, these drivers have to be both kept alert during their ride and must have good sight on the road. Therefore the method is characterized in that the output fraction of melatonin suppressive radiation is>=0.45 Melatonin Watt/Watt and that the light output is<=10 lumen/Watt. The low light output of<=10 lumen/Watt facilitates to relatively easily obtain a lighting level inside the cabin of the truck that is sufficiently low not to form a disturbance for the truck driver. Thus the truck driver is enabled both to stay awake and to have a good view on the road.

In circumstances that people have to be kept alert and vision conditions are determined only by a relatively simple task, melatonin suppressive radiation together with a sufficiently amount of visible light can be administered. Examples of such circumstances are outdoor container work activities in a shipyard, which work only requires that articles can be distinguished by their shape and/or text. For these circumstances an embodiment of the method is characterized in that the output fraction of melatonin suppressive radiation is>=0.45 Melatonin Watt/Watt and the light output is>=60 lumen/Watt.

In circumstances that people have to be kept alert and good colour vision conditions are necessary to carry out the task, melatonin suppressive radiation together with relatively high amounts of visible light can be administered. Examples of such circumstances are shift work, first aid centers in hospitals. For these circumstances an embodiment of the method is characterized in that the output fraction of melatonin suppressive radiation is>=0.45 Melatonin Watt/Watt and the light output is>=100 lumen/Watt, the light source having a color rendering index (CRI)>=65. Other examples for melatonin suppressive lighting methods are in schools, universities, libraries in classrooms, lecture halls, conference rooms. Preferably an embodiment the method is characterized in that the output fraction of melatonin suppressive radiation is>=0.6 Melatonin Watt/Watt and the light output is>=100 lumen/Watt, the light source having a color rendering index (CRI) >=65 and a color temperature of>=6500 K. This method is appropriate for people not having options to catch sufficient daylight for example in the winter period, or elderly people with disturbed rhythms, or people with Monday morning hangover. The color temperature is relatively high which has a supporting psychological effect on the alertness next to the effect on alertness by melatonin suppression. Light having the properties of>=0.45 Melatonin Watt/Watt and>=100 lumen/Watt is obtainable by a single light source but alternatively is obtainable by combinations of light sources. In these combinations a first light source having a relatively high lumen output, for example a/80 low-pressure mercury discharge fluorescent lamp with >=200 lumen/Watt and a color rendering index (CRI) of>=80, is combined with a second light source having a relatively high melatonin suppressive radiation output, for example a /03 low-pressure mercury discharge fluorescent discharge lamp with>=0.7 Melatonin Watt/Watt. Such combinations enable the addition of, for example, second light sources to an existing lighting system having only first light sources, to obtain the suitable light radiation. The lighting system thus obtained has a light source yielding the suitable light radiation and has the advantage that it is relatively cheap.

In the case visual conditions are demanding, for example work for some hours in the evening, and sleep quality should not be decreased and thus to reduce the risk on making mistakes the day after, light should be provided that influences the melatonin cycle to a relatively small degree. For these applications the method of the invention is characterized in that the output fraction of melatonin suppressive radiation is<=0.2 Melatonin Watt/Watt and the light output is>=100 lumen/Watt, the light source having a color rendering index Ra >=65, preferably the output fraction of melatonin suppressive radiation is<=0.1 Melatonin Watt/Watt. Such applications can be found for people who wake up shortly in night hours or need to be inspected during night hours for example at home for elderly but also for parents with young kids, elderly homes, hospitals, nursing homes. In these cases the melatonin non-suppressive light for the 'sleepers' can be combined with alerting light for the 'watchers' in their working/observation room. Such types of light can be special nightlights, optionally integrated in bed head-units, orientation lights in halls, doorways, stairs.

In an embodiment, the method is characterized in that the output fraction of melatonin suppressive radiation shifts from>=0.45 Melatonin Watt/Watt to<=0.2 Melatonin Watt/Watt or vice versa and the light output is>=100 lumen/Watt, the light source having a color rendering index Ra>=65. Via this method a controlled gradual change from melatonin suppressive radiation to non-suppressive radiation is obtainable whereby also continuously sufficient light is provided, enabling people to work correctly. This method is usable for example in light for people working in fast rotating shifts, eventually starting with a short period with suppressive light and ending with a period with non-suppressive light to accommodate easy sleep onset after the night shift and prevent any phase shifting of the biological clock. The method involving a shift from melatonin non-suppressive to suppressive radiation, depending on time of day, is usable in applications to re-synchronise biological clock in the case of travelling over various time zones, i.e. jet-lag.

Lighting systems having a light output of>100 lumen/Watt, a color rendering index (CRI)>=65 and the possibility to shift from melatonin suppressive radiation output of>=0.45 Melatonin Watt/Watt to<=0.2 Melatonin Watt/Watt, may contain a single light source but alternatively may contain first and second light sources. In the embodiment of the lighting system containing a single light source, the output of the single light source is adjustable, for example by adjusting the lamp voltage. An example of such a light source is an electrodeless low-pressure mercury discharge fluorescent lamp (QL). In the embodiment of a lighting system containing first and second light sources, the lighting system shifts from use of the first light source to use of the second light source or vice versa. In the lighting system the first light source has a relatively high melatonin suppressive radiation output, for example a high-pressure mercury discharge lamp with>=0.45 Melatonin Watt/Watt, and the second light source has a relatively low melatonin suppressive radiation output, for example a white high-pressure sodium discharge lamp with<=0.15 Melatonin Watt/Watt. Both light sources having a light output of>=200 lumen/Watt and a color rendering index (CRI) of>=65 during nominal operation.

Alteratively, in an embodiment of the invention, the method is characterized in that filtering means are used for adjusting the suitable light radiation to be received by the human subject. Via this method melatonin suppressive radiation can be administered to the human subject while admission of this radiation to the eye can be chosen as desired. It is thus possible for persons to operate in the same environment of which one person should stay awake by interrupting his melatonin built-up, and for another person without interrupting his melatonin built-up.

The present invention further relates to methods for the adjustment of the circadian pacemaker by the administration of light to the subject.

All vertebrates exhibit temporal organization in their activities. Preferred vertebrates for use of this method are mammals and, in general, it will be appreciated that it is particularly preferred to treat humans. For example, man is naturally diurnal, sleeping through the night and active during the day. Such patterns of activity are not, however, fixed, and it is possible to adjust this circadian rhythm. Adjustment of the circadian rhythm is not without its problems, and can take several days during which the individual has to adjust, depending on both the amplitude of the displacement of the circadian axis and the individual concerned. During the adjustment, the individual typically exhibits wakefulness during desired sleeping periods and, concomitantly, drowsiness during desired waking periods. Even when fully awake, if the individual is still adjusting, clumsiness and inefficiency are commonplace.

In humans, adjustment, or realignment, of the circadian pacemaker, which is responsible for determining the circadian rhythm of the individual, is common. For example, shift workers, trans-meridian travellers, the aged and people suffering from affective disorders are all capable of benefiting from circadian pacemaker realignment. Although some animal studies have addressed the issue of the spectral composition of the light needed to affect the circadian system, few studies have been conducted in humans. Using single irradiances of monochromatic light, Brainard and colleagues [Ann. N.Y. Acad. Sci., 453 (1985) 376-378] concluded that light of 509 nm was more effective than 448, 474, 542, 576 and 604 nm light.

WO98/51372 (Campbell) discloses a method for resetting a circadian clock in humans, which comprises the administration of non-solar light to a non-ocular region of the human body, optionally during sleep.

U.S. Pat. Nos. 5,176,133, 5,167,228 and 5,163,426 (Czeisler) all disclose methods for accurately assessing and rapidly modifying the phase and amplitude of the endogenous circadian pacemaker over a period of at least 36 hours, generally involving several hours exposure to bright light. It is believed that the reason why the prior art indicated that a wavelength of about 509 nm was the most effective at suppressing the production of melatonin was because of the problem of experimenting with human subjects. Typically, a single dose of light was applied, without obtaining a baseline reading, and the effect on reduction of melatonin expression was measured.

It will be appreciated that the light administered to the subject need not be restricted to the preferred wavelength. However, it is essential that there be sufficient of the necessary wavelengths in the light administered to the subject in order to effect melatonin suppression.

In general, the lux level of the light source, where substantially monochromatic light is used, should be in the region of 40 lux or greater for wavelengths below 480 nm. General lux levels of up to 100,000 (equivalent to bright daylight) are feasible, but higher lux levels can not only be uncomfortable for the subject, but can also be expensive to produce and consume large amounts of power. Accordingly, it is preferred to provide lux levels of between about 60 and 500 lux, with levels between 70 and 300 being more preferred. Appropriate levels may be between about 80 and 150 lux.

Duration of administration of light will be determined by many factors, including the state of the individual, the magnitude of the adjustment to the circadian pacemaker and the desired result. In general, administration of light should occur when the subject is not otherwise exposed to bright daylight and at times when melatonin production is occurring, about to occur or just terminated Peak production is generally between 01.00-05.00 hours. Administration in the period leading up to this and during this peak can shift the circadian rhythm substantially forward, i.e. delay it. Likewise, administration of light after this peak can bring the rhythm back, so that either can be chosen in order to assist with trans-meridian travel or adaptation following shift work.

Whilst the above are guidelines, it will be appreciated that other regimes may better serve to compensate the circadian rhythms of trans-meridian travellers or shift workers. Other conditions may be treated as deemed appropriate either by the subject or by a responsible clinician. For example, seasonal affective disorder (SAD) is experienced by many during the winter months. Whilst this invention is not bound by theory, it is likely that these people either do not experience sufficient direct sunlight during these periods, or are not sufficiently sensitive to the amount of sunlight present during these months, or their circadian rhythm is either insufficiently robust so that, during winter months, the rhythm loses definition or is abnormally long or delayed. Whatever the reason, supplemental light of the invention during daylight hours, especially in the morning and evening serve to redefine the subject's circadian rhythm and alleviate the disorder.

Surprisingly, the present invention is also particularly useful for the aged. It is common for the circadian rhythm of the elderly to be less robust, with substantial periods of wakefulness during the night, and periods of drowsiness during the day.

Receptiveness to short wavelengths is substantially reduced in the elderly through aging effects on the lens and cornea. Thus, treatment with enhanced levels of short wavelength radiation, in accordance with the present invention, serves to redefine and strengthen the circadian rhythm in the elderly, thereby allowing them to lead more normal lifestyles. The treatment for elderly patients is similar to that for those suffering SAD, but intensities are typically higher, so that lux levels of between 200 and 1000, more typically between 200 and 600 and, usefully, up to about 400, may be employed. Lux levels at the lower end of the preferred ranges may be employed where the short wavelength light is deployed in the vicinity of elderly people during a substantial proportion of normal daylight hours. Suitable levels will be readily determined by carers, for example.

Blind people may also benefit from the present invention, with light either applied directly to the eyes or other parts of the body. It will be appreciated that treatment will be highly dependent on the nature of the blindness in question.

As noted above, the wavelength of the light is greater than ultraviolet, although the present invention envisages wavelengths in the broader region with ultraviolet. In general, though, ultraviolet light should be avoided, in order to minimize risk to the subject.

The present invention will now be illustrated by the following, non-limiting Example.

EXAMPLE

Of each subject the fluence response curves for individual, monochromatic wavelengths are established. These are obtained by first measuring a baseline for each light treatment, and then administering different amounts of a given wavelength of light to the subject, at a specified time, in order to be able to establish a dose response curve for each wavelength studied. This allows $ED_{50}$ readings to be obtained from each dose fluence response curve. From this, we have established that the effective wavelength for suppressing melatonin production is substantially lower than expected, in the region of 400 to 460 nm.

A) Methods

The wavelength study was conducted in study legs, each of which consisted of three consecutive nights. The first night was a baseline night followed by two light exposure nights. In total, twenty study legs were conducted and each subject completed between one and sixteen legs. Three or four study legs, when conducted consecutively, made a study session.

| | |
|---|---|
| Study night | 19:00-07:00 h |
| Study leg | 3 consecutive study nights |
| | Night 1 - baseline |
| | Night 2 - light treatment 1 |
| | Night 3 - light treatment 2 |
| Study session | 3-4 consecutive study legs every week or every other week |

Twenty-two subjects (4 F; 18 M) were selected, ranging in age from 18-45 years (mean±SD=27±7 years). Subjects were healthy adults under no medication except minor analgesics or the oral contraceptive pill. Three days before the tests, subjects were required to keep a regular sleep wake cycle and were asked to retire to bed at 23.00 h and arise at 07.00 h.

Study Nights

Test protocol started at 19.00 h. An indwelling cannula was placed in the subject's forearm. From 21.00 to 23.00 h the subjects were kept in dim light (<10 lux). Ninety minutes before the light treatment a single drop of pupil dilator Mimins Tropicamide 0.5% (Chauvin pharmaceuticals, Romford, UK) was placed in each eye. Immediately after insertion of the pupil dilator, subjects were asked to wear eye masks and lie in a semi-recumbent position. At 23.00 h the room lights were turned off and all subjects lay in a semi-recumbent position in complete darkness wearing eye masks.

Subjects were given 30 minutes of light treatment at a set time between 23.30 and 02.30 h. The time of light treatment was individualised to occur on the rising slope of the endogenous (natural) melatonin rhythm, before melatonin peak production. Blood samples were taken at −90 minutes just before administration of the pupil dilation and then at 15 minute intervals, 15 minutes before the light exposure to one hour after lights off and then a final sample at a 30 minute interval. Blood samples were collected into lithium heparin tubes and centrifuged for 10 minutes at 3000 rpm. Plasma was separated and stored at −20° C. until assayed.

Each different light treatment was given for 30 minutes at various times between 23.30 and 02.30 h to between 3-7 subjects. Subjects were asked to place their heads in a light sphere (infra) and position themselves correctly by placing their chin on the chin rest and head against a headband. The chin rest was adjusted so that the individual's eyes were positioned at the level of the center line. They were asked to keep their eyes open and fix their gaze at a point marked in the back center of the sphere.

A summary of light treatments is given in Table 1, below.

For the light treatment, subjects placed their heads in a 45 cm diameter sphere (Apollo Lighting, Leeds, UK). The sphere had an opening cut in order to accommodate a subject's head. The inside of the sphere was coated with 8 coats of white reflective paint (Kodak White Reflective Coating, Integra Biosciences Ltd., Letchworth, Hertfordshire, UK) to give a 96% reflective surface (Macam Photometrics Ltd., Livingstone, Scotland, UK). An adjustable chin rest was built in house and painted with the reflective coating. This, together with a headband, was fitted to the sphere.

TABLE 1

| Wavelength (nm) | Irradiance (µW/cm$^2$) | Number of subjects (N) |
|---|---|---|
| 424 | 1.9 | 6 |
|  | 2.8 | 6 |
|  | 4.5 | 6 |
|  | 9.0 | 6 |
|  | 11 | 5 |
| 456 | 2.0 | 5 |
|  | 4.0 | 5 |
|  | 8.0 | 5 |
|  | 29 | 4 |
| 472 | 1.8 | 6 |
|  | 2.8 | 7 |
|  | 4.1 | 6 |
|  | 9.0 | 6 |
|  | 14 | 6 |
|  | 22 | 6 |
|  | 31 | 5 |
| 496 | 3.0 | 4 |
|  | 6.5 | 7 |
|  | 13 | 6 |
|  | 18 | 6 |
|  | 26 | 5 |
|  | 30 | 5 |
| 520 | 0.7 | 3 |
|  | 1.8 | 6 |
|  | 3.3 | 3 |
|  | 4.1 | 5 |
|  | 7.0 | 7 |
|  | 16 | 6 |
|  | 27 | 5 |
|  | 41 | 6 |
|  | 65 | 5 |
| 548 | 7.2 | 5 |
|  | 14 | 5 |
|  | 26 | 3 |
|  | 52 | 3 |
|  | 65 | 5 |
| White | 2.2 | 3 |
|  | 3.9 | 6 |
|  | 6.6 | 4 |
|  | 7.2 | 5 |
|  | 91 | 8 |

This light sphere provides uniform illumination of the entire retina in a pupil-via dilated individual. The sphere was illuminated via fibre optic cable, which was attached to the top of the dome at a 20° angle. This cable was connected to the light source, which was provided by a metal halide arc lamp (Enlightened Technologies Associates Inc., Fairfax, Va., USA).

Four different light boxes are used in the experiments. Light boxes A and B use a 21 Watt (W) miniature metal halide arc lamp developed by Welch-Allyn. light boxes C and D use a 50 W miniature metal halide arc lamp also developed by Welch-Allyn. Each light box contains a heat mirror between the light source and the fibre optic cable, to ensure Ultraviolet (UV) and infrared (IR) radiation is filtered out (Enlightened Technologies Associates Inc., Fairfax, Va., USA).

In later experiments (Study legs 17-20), which required higher light irradiances, two fibre optic cables from two light boxes were fed into one sphere by adapting the input port.

All light sources showed no UV emission when tested with a UV radiometer (UVP Inc., San Gabriel, Calif., USA). Light sources were also tested for electromagnetic field (EMF) generation. All light treatment conditions showed no EMF greater than a background level of 0.1 µT.

Monochromatic filters at six different wavelengths of maximum transmission ($\lambda_{max}$) (430 nm, 460 nm, 480 nm, 500 nm and 560 nm (Half maximal bandwidth $\lambda_{1/2}$=10 nm)(Coherent Ealing, Watford, Herts.UK) were placed in the input port of the sphere. The intensity of the monochromatic light was adjusted using combinations of Kodak Wratten neutral density filters (Richard Frankfurt, Croydon, Surrey, UK) which were also placed in the input port of the sphere between the light probe and the sphere.

The set up of the light source altered the spectral quality of the monochromatic light slightly and measurements with a spectrophotometer (Spectrascan 650 portable, Photoresearch, Chadsworth, Calif., USA) confirmed the actual wavelengths at eye level. The $\lambda_{max}$ of these were 424 nm, 456 nm, 472 nm, 496 nm, 520 nm and 548 nm ($\lambda_{1/2}$5-13 nm).

Light was measured at subjects' eye level using a portable radiometer (Macam Photometrics Ltd., Livingstone, Scotland, UK). It was noted that even if the detector was turned at right angles the irradiance did not change. Irradiance measured in µW/cm$^2$ was then converted to the number of photons by the calculations described below.

The spectral characteristics of the monochromatic light were also measured at the subjects' eye level to determine the percentage transmission of light at each wavelength through the filter. This was done so that if the sphere or fibre optic cable changed the spectral characteristics of the filters then this could be accounted for in the photon calculations.

In order to calculate the number of photons in a given irradiance of monochromatic light the measured irradiance and the energy/photon for each nanometer of light is used.

photons/cm$^2$/s=irradiance (µW/cm$^2$)/energy of 1 photon at wavelength

The energy of 1 photon of for example 500 nm light, can be calculated by the following equation:

$$E=hV$$

$$h=\text{Plank's constant } (6.625 \times 10^{-34} \text{ watts/s}^2)$$

$$V=\text{frequency of wave } C/\lambda \text{ ((speed of light (C)=3.00} \times 10^{17} \text{ nm/s)} \lambda)$$

Therefore, if 3 µW/cm$^2$ of 500 nm of light is measured the number of photons is calculated as follows:

First, the energy in 1 photon of this light is calculated $$E=hV \;(V=C/\lambda)$$

$$E=(6.625 \times 10^{-34} \text{ watts/s}^2) \times (3.00 \times 10^{17} \text{ nm/s})/500 \text{ nm})$$

$$E=3.975 \times 10^{-13} \text{ µW/photon/s}$$

Thus at an irradiance of 3 µW/cm$^2$ $$\text{Number of photons/cm}^2/\text{s} = (3 \; \mu W/cm^2)/(3.975 \times 10^{-13} \mu W/\text{photon/s})$$

$$= 7.5 \times 10^{12} \text{ photons/cm}^2/\text{s}$$

In order to calculate the total number of photons given for 30 minutes of light exposure, the total number of seconds are calculated=30×60=1800 seconds $$\text{Total number of photons} = (7.5 \times 10^{12} \text{ photons/cm}^2/\text{s}) \times (1800)$$

$$= 1.35 \times 10^{16} \text{ photons/cm}^2$$

The manufacturer provided the % transmittance for each monochromatic filter. The total photons were calculated by adding the photons/cm$^2$/s transmitted at each 10 nm wavelength. For example, if a 500 nm filter only transmits 50% at 500 nm and 1% at 490 nm and 1% at 510 nm then, in order to calculate the photons of the measured light, which consists of 96% 500 nm and 2% each of 490 nm and 510 nm, photons/cm$^2$/s were calculated as described above and multiplied by the actual percentage transmittance. The photons/cm$^2$/s at each 10 nm wavelength were then summed to give the total number of photons/cm$^2$/s for the measured irradiance. This value was corrected for the duration of light exposure. For all calculations, the real measured photons were used.

Plasma melatonin levels were determined by direct RIA (Radioimmunoassay). All plasma samples for each subject for each leg were measured in the same assay. Samples were assayed in night sequence (i.e. 23.00 n1, n2, n3 and then the next time point for all three nights) to minimize any effect of assay drift on the measurements. The RIAcalc program determines the percentage of total counts bound or free, and then plots them as a function of known concentrations of the melatonin standards. A smooth curve is fitted through the standard points and the concentrations of the unknown samples are determined from this curve.

Data Analysis

For each light treatment for each individual, each time point was expressed as a percentage of the corresponding baseline time point. At each irradiance studied the individual data were averaged for each time point. Paired Students't test checked for significant differences between the baseline night and the light treatment night at each time point. These data showed that maximum melatonin suppression occurred around 30-45 minutes after lights on. Therefore these two points were used in the calculation of melatonin suppression.

Light-induced suppression of plasma melatonin was calculated by comparing the average of the point at 30 and 45 minutes after lights on, on the light treatment night (N2) to the same values for the baseline night (N1) for each individual as follows:

$$\% \text{ melatonin suppression} = \frac{(N1_{(mean\ 30+45mins)} - N2_{(mean\ 30+45mins)})}{N1_{(mean\ 30+45mins)}}$$

Data from all the subjects receiving the same light treatment were averaged (arithmetic mean). The individual data were log transformed and then averaged. Retransforming the values produced the geometric means±variance.

Irradiance response curve fitting. For each wavelength irradiance response curves were plotted (photons/cm$^2$ against % melatonin suppression). Best fit curves were generated (SAS 6.12) using the four-parameter logistic equation described below.

$$y = \frac{a-c}{\left(1 + \left(\frac{x}{b}\right)^d\right)} + c$$

y=% melatonin suppression
a=response when Irradiance (I)=0
c=response when (I) is maximum
x=total number of photons
b=half saturation response
d=slope of line B) Results The method of the invention is best understood and appreciated by referring to the accompanying drawing, in which:

FIG. 1 Irradiance response curves using the four parameter logistic equation;

FIG. 2 For each wavelength, the 50% calculated maximal sensitivity (σ) plotted relative to 456 nm, the action spectrum;

FIG. 3 The best fit of the action spectrum of FIG. 2;

Figure 1:
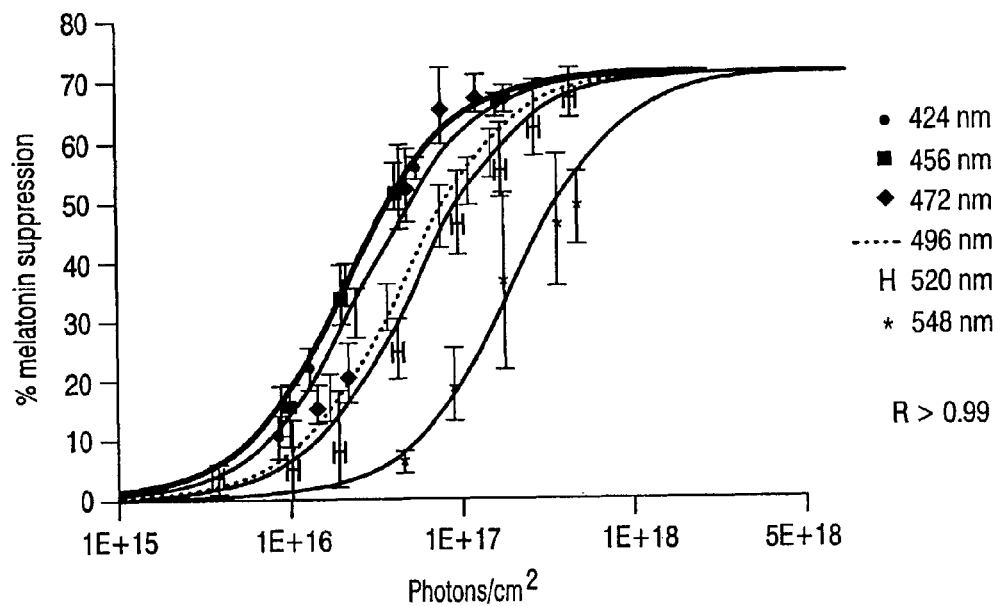

Irradiance response curves using the four parameter logistic equation were constructed for each wavelength using zero as the response for zero irradiance (a) (FIG. 1). A range of values were used for the maximum response (c) and the slope (d) was fixed and left free for these calculations. The best fits to the data were achieved when the maximum response was fixed at 70 (r values≧0.99). The slope was fixed at 1.5. Therefore, the equation used at this maximum was as follows:

$$\text{Measured and calculated suppression} = \frac{0 - 70}{1 + (I/\sigma)^{1.5}} + 70$$

Where I=total number of photons
σ=half saturation constant

Figure 2:
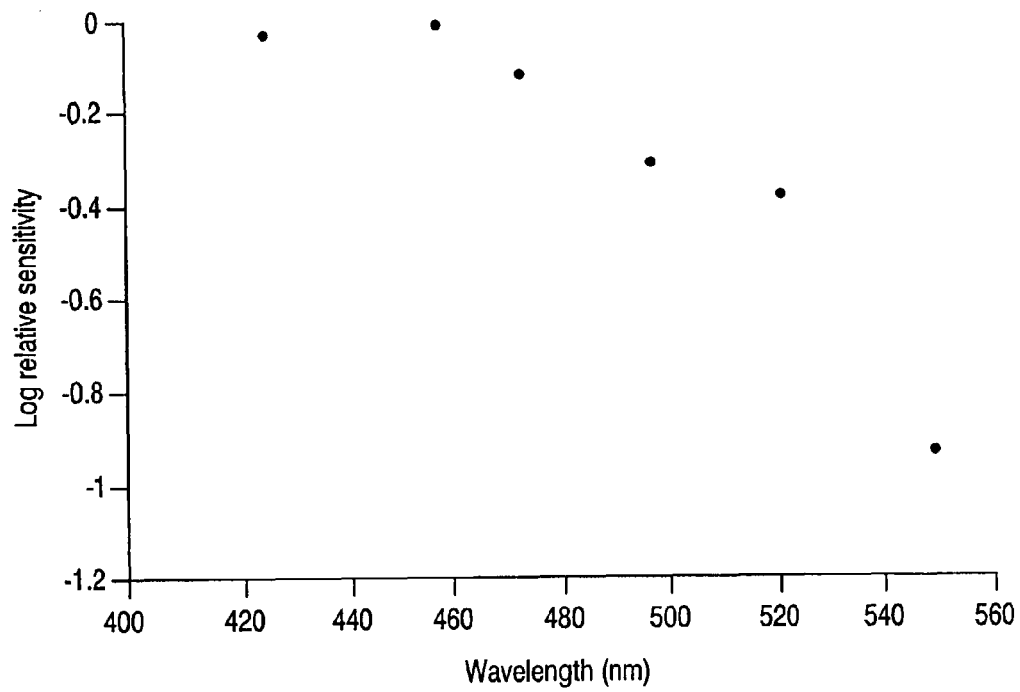

For each wavelength, the 50% maximal sensitivity (a) calculated from the fitted lines was: 1.86×10$^{16}$ photons/cm$^2$ at 424 nm, 1.79×10$^{16}$ photons/cm$^2$ at 456 nm, 2.29×10$^{16}$ photons/cm$^2$ at 472 nm, 3.60×10$^{16}$ photons/cm$^2$ at 496 nm, 4.23×10$^{16}$ photons/cm$^2$ at 520 nm light and 1.49×10$^{17}$ photons/cm$^2$ at 548 nm. These data were then plotted relative to 456 nm (FIG. 2).

Figure 3:
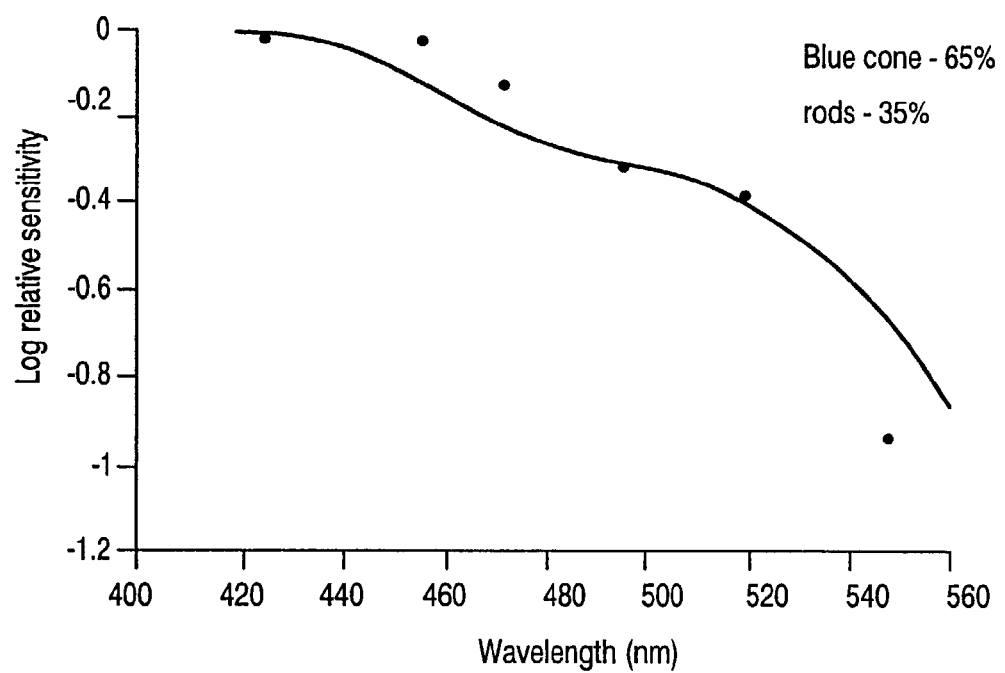

The action spectrum (FIG. 2) was then fitted using nomograms generated using Dartnall's nomogram for the four known photoreceptors. Individual nomograms for the rod (500 nm) receptor, blue (420 nm) cone, green (535 nm) cone and red (560 nm) cone were generated and combinations of different ratios were used to match with the observed melatonin suppression action spectrum. The best fit was obtained using 65% blue cone and 35% rod receptor (FIG. 3).

The results indicate that, of the known photoreceptors, the blue cone ($\lambda_{max}$ 420 nm) has the greatest involvement in the suppression of melatonin. Compared with 424 nm light, about twice the number of photons of 496 nm light (rod photoreceptor $\lambda_{max}$) are required to produce equivalent suppression. More than 2.2 times as many photons are required of the 520 nm wavelength to produce the same effect. Approximately 8 times more light is needed in the 548 nm range for the same effect, implying that red cones have a minimal influence in this system.

Figure 4A:
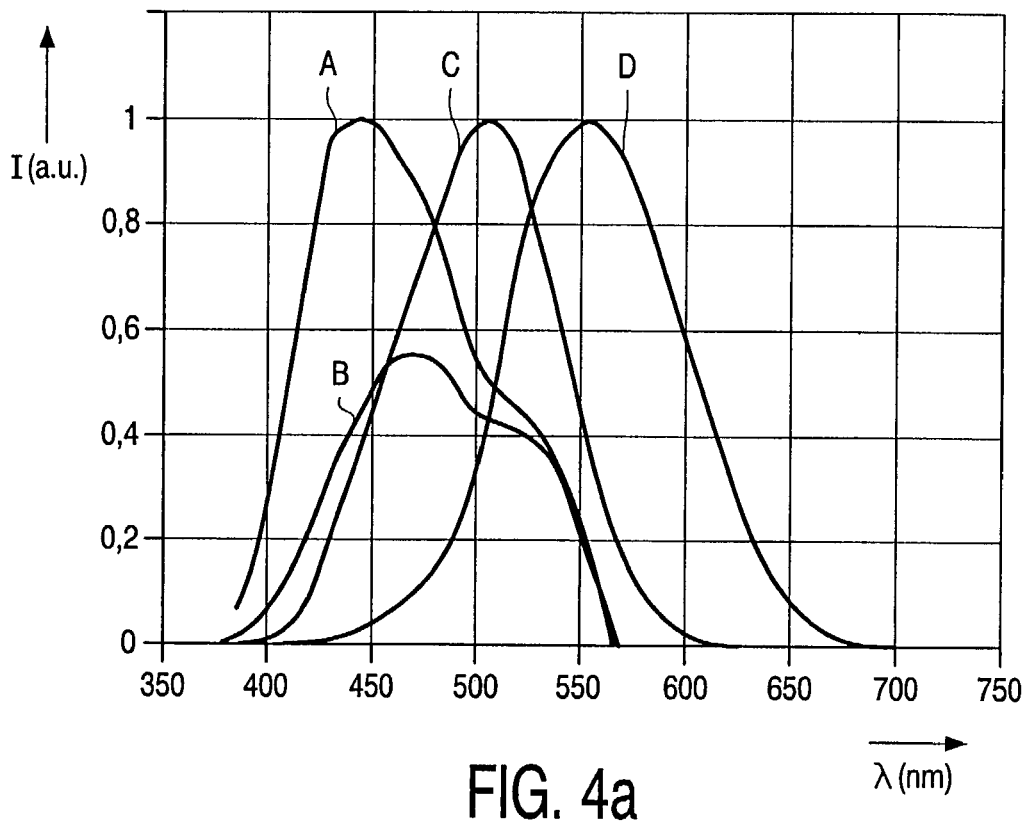
FIG. 4a shows the wavelength-dependence I on a relative scale of melatonin suppression for young people (graph A) and for older people, lens corrected (graph B) and the curves for scotopic (graph C) and photopic vision (graph D)

FIG. 4a shows sensitivity graphs on a relative scale, i.e. the maximum value for each independent sensitivity graph is set to 1, of scotopic night-vision (graph C), normal colour photopic vision (graph D), and typical melatonin suppression corrected for lens transmittance for young (20-40 years, graph A) and elderly (>=60 years, graph B) people. FIG. 4a clearly shows that the melatonin suppression sensitivity, compared with the photopic sensitivity and even compared with scotopic sensitivity, is shifted towards a shorter wavelength region. The sensitivity for the melatonin suppression peaks between 400-460 nm, with decreasing efficacy to about zero at 560 nm, the wavelength of 560 nm being close to a maximal sensitivity for photopic vision at 555 nm. The photopic vision (eye sensitivity flux) has a value of 683 lumen obtained by 1 Watt of light having a wavelength of 555 nm. FIG. 4a further shows that the melatonin suppression sensitivity via the eye of elderly people is significantly decreased and that its maximum sensitivity is shifted towards a longer wavelength, i.e. to a wavelength of about 475 nm.

Figure 4B:
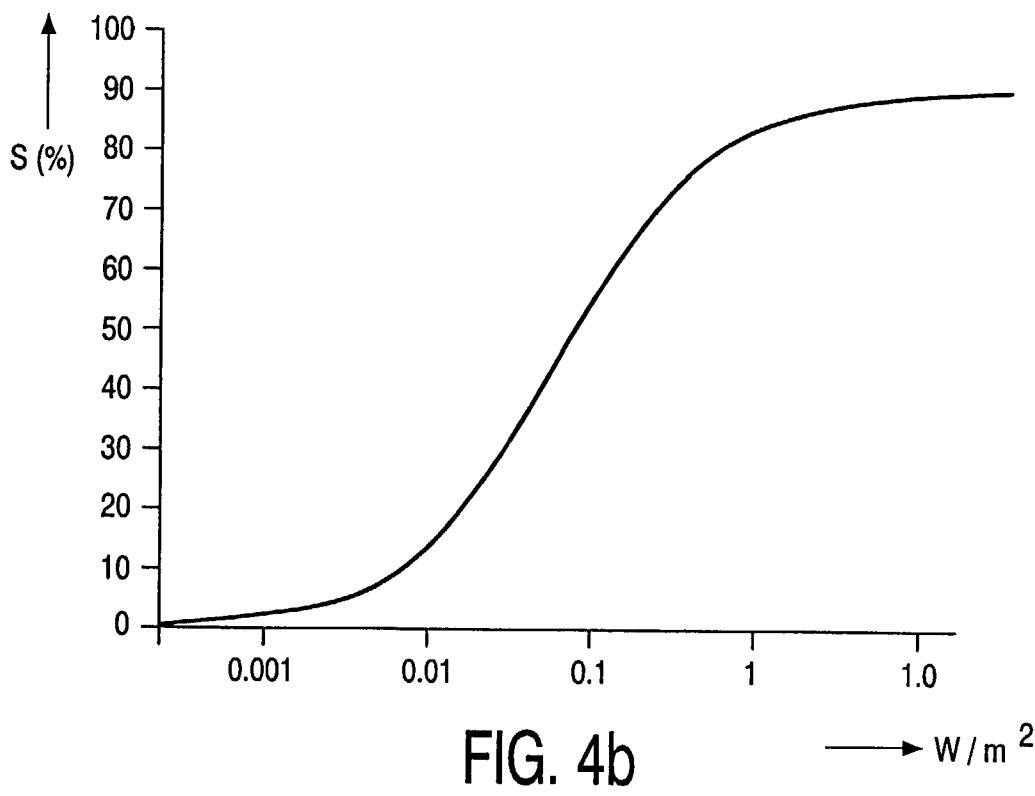
FIG. 4b shows the degree of melatonin suppression S on a relative scale in dependency on the density of radiation in Watts per m$^2$ with a wavelength of 500*10$^{-6}$ m (=500 nm)

FIG. 4b shows the relationship between the degree of melatonin suppression and the radiation density in W/m2 for an exposure time of 30 minutes. The curve for a wavelength of 500 nm is given, the dependency on other wavelengths is similar, for 420-490 nm the curves are shifted to lower radiation densities, for 510-560 nm, the curves are shifted to higher radiation densities. About 50% melatonin suppression occurs at about 0.08 W/m2 in the case of a fully dilated pupil.

Figure 5:
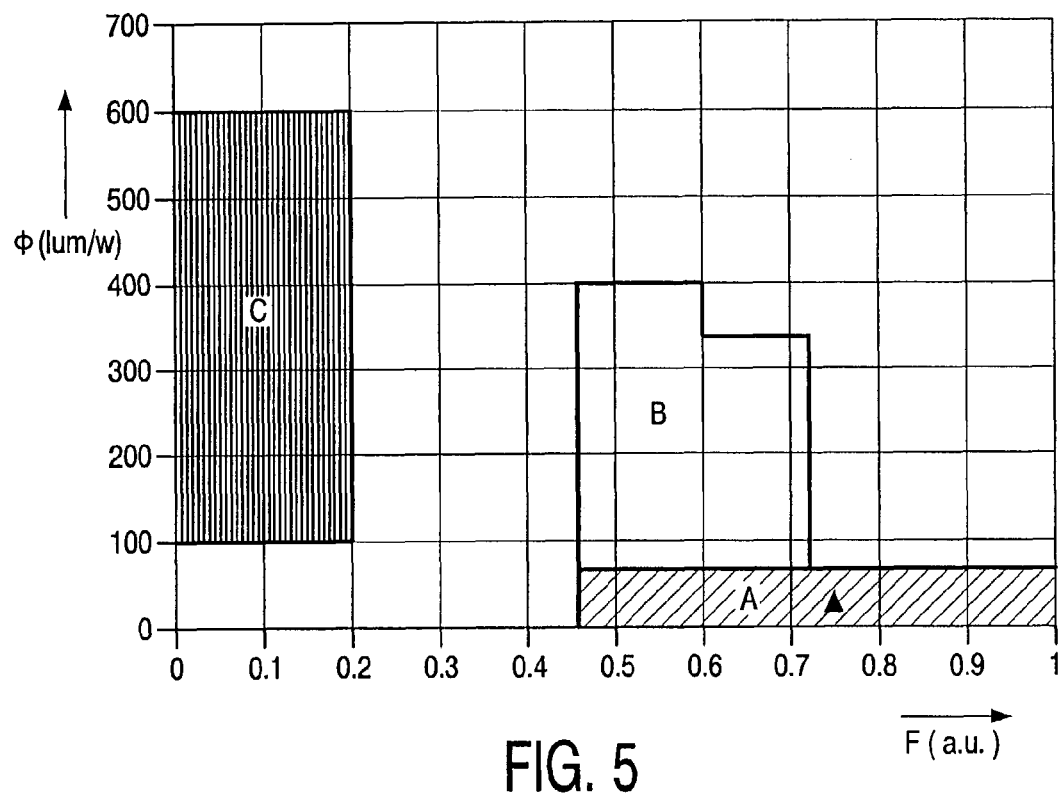
FIG. 5 shows a diagram with three main areas A, B, and C of suitable radiation for controlling the awareness of a human subject, the x-axis representing the fraction F of melatonin Watt per Watt and the y-axis representing the luminous flux per Watt, the triangle representing a/03-low-pressure mercury discharge fluorescent lamp.

FIG. 5 shows a diagram with areas of suitable radiation for attaining the various desired effects on the melatonin cycle. Three areas, i.e. A, B and C, are distinguished. In Area A the light has a very high melatonin suppression with a low lighting level, melatonin Watts/Watt 0.45 and 1 m/Watt lower than 60 or even lower than 20. In area B the light has a high melatonin suppression with an acceptable to high lighting level. Main characteristics for this area B are melatonin Watts/Watt>=0.45 with 1 m/Watt>=60. A split up can be made between white, whitish and colored light sources. Basic benefits are better lighting conditions with almost the same melatonin suppressing capacity as in area A. In area C the light has a low melatonin suppression and a high lighting level. Main characteristics for this area C are melatonin Watts/Watt<0.2 (and/or resp.<=0.1 melatonin Watts/Watt) with various 1 m/W>=100. Also in this area a distinction can be made between white, whitish and colored sources.

For the treatment of a human subject with the method according to the invention, the method roughly may comprise the following steps:
  determining the phase of the cycle of the human subject;
  estimating a desired effect on the cycle of the human subject;
  determining surrounding light radiation effects on the cyclic melatonin variation of the human subject;
  determining desired light radiation (spectrum, intensity, exposure period, and interval period) for suppressing or allowing the melatonin built-up or stimulating the melatonin degradation, resp. choosing a light source with a light radiation output according to one of the areas A, B or C.
  exposing the human subject during an exposure period to the suitable light radiation without substantially influencing the phase of said cycle, optionally while screening of ambient light radiation, the suitable light radiation being specified by an output fraction of melatonin suppressive radiation (Melatonin Watt/Watt) and light output (lumen/Watt), the output fraction and light output being adjusted to obtain the desired effect on the phase of said cycle.

Figure 6:
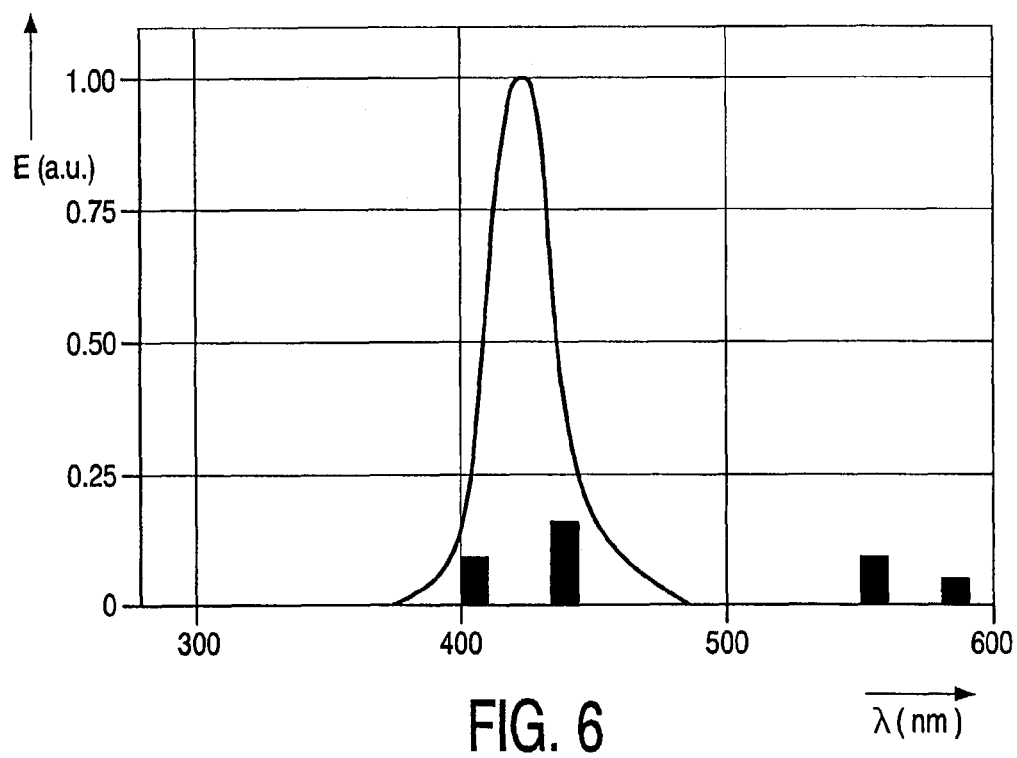
FIG. 6 shows an emission spectrum of a low-pressure mercury discharge lamp suitable for melatonin suppression at a low lighting level, the x-axis representing the wavelength X and the y-axis representing the relative emission intensity E.

FIG. 6 shows an emission spectrum of a low-pressure mercury discharge lamp being part of a system with a nominal power of 15 Watt, of which effectively about 20% is converted into radiation, the lamp having an internal coating of SPE (strontium pyrophosphate activated with $Eu^{2+}$). Normally the lamp is used for photocopying. However, it is very appropriate for use in the method according to the invention as the emission spectrum of the lamp peaks at about 420 nm, at or close to the maximum of the melatonin suppression sensitivity. The lamp is effectively usable in the method according to the invention, as it is very suitable for suppressing melatonin at a low lighting level. The method is effectively used when an exposure time of 30 minutes is applied to the human subject with (dark) interval periods, i.e. periods when the lamp is out of operation, of about 30 minutes. Said method find its application in activities in which a low lighting level is needed but in which activities require that people has to be kept alert and awake, for example in control rooms of an air field or in a cabin or a truck for truck drivers at night. When a cabin of a truck is provided with said system of 15 W comprising said lamp, in the cabin a lighting level of about 3 lux and a melatonin suppressive radiation intensity of about 0.08 $W/m^2$ is obtained. The lighting level of 3 lux corresponds to a dim lighting level. The melatonin suppressive radiation intensity of about 0.08 $W/m^2$ is a suitable value for suppression of melatonin of about 50%. The emission spectrum of the lamp has some undesired radiation, see FIG. 6. For a small part it has undesired radiation in the ultraviolet region, i.e. at shorter wavelengths than 380 nm, and in beyond the blue-green region, i.e. at wavelengths longer than 540 nm. This undesired radiation can be eliminated relatively simple by using appropriate filters. For example the lighting level caused by emission in beyond the blue-green region, can be decreased very simple, for example by an absorption filter having a bandedge at about 510 nm. By this filter the lighting level is decreased down to about 1 lux, which is an appropriate light level for truck cabins. The filter leading to only a relatively small decrease in the melatonin Watts/Watt.

Figure 7:
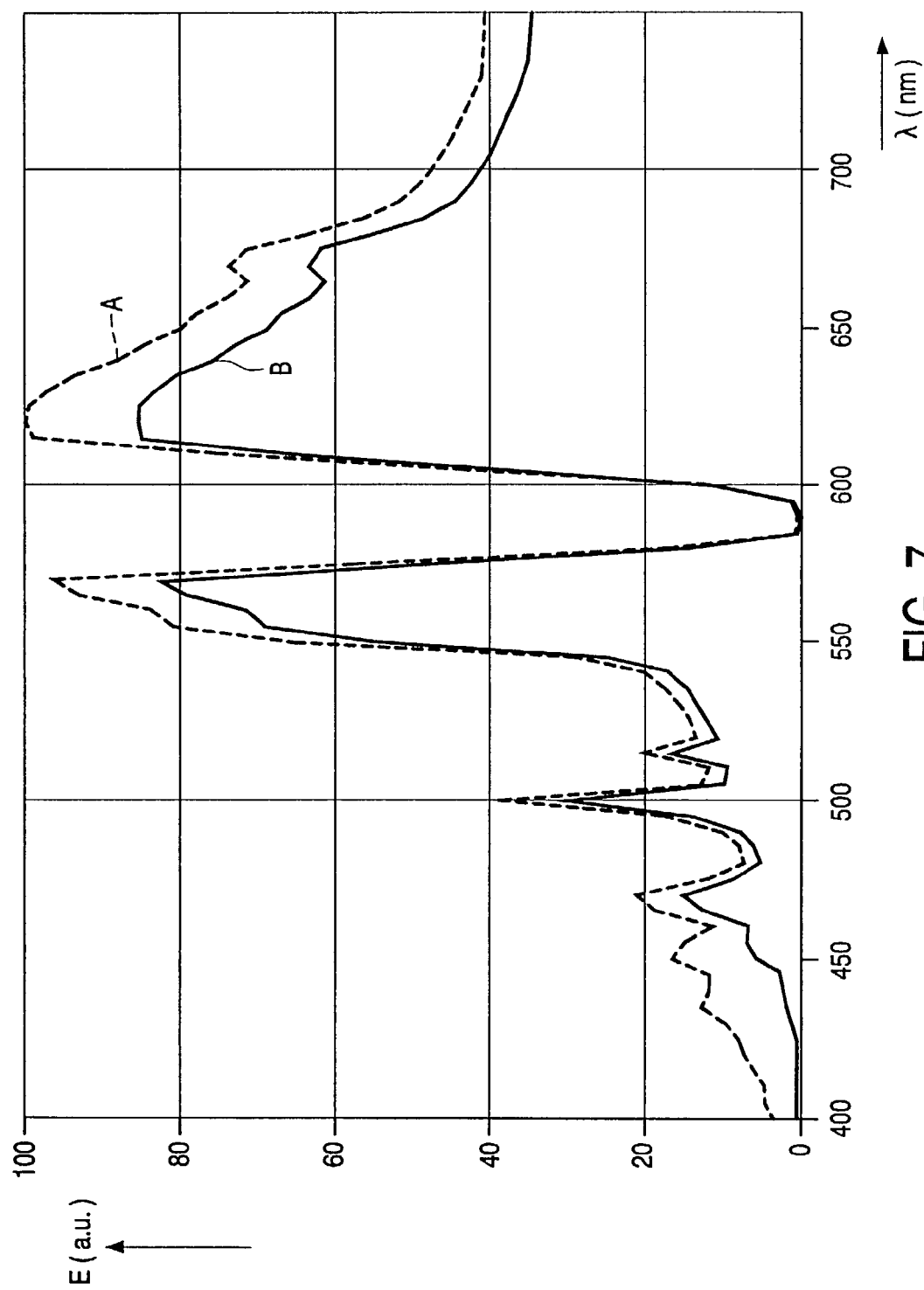
FIG. 7 shows emission spectra of a 'white'-high-pressure sodium discharge lamp without a filter (graph A) and with filter (graph B), the x-axis representing the wavelength λ and the y-axis representing the relative emission intensity E.

FIG. 7 shows the emission spectra of "white"-high-pressure sodium discharge lamps A and B, respectively without filter (graph A) and with filter (graph B). The filter is a generally available absorption filter with an absorption edge at 460 nm. The lamp with filter, i.e. lamp B, has suitable light radiation with an output fraction of melatonin suppressive radiation of about 0.09 Melatonin Watt/Watt. The lamp without filter, i.e. lamp A, has a significantly higher output fraction of melatonin suppressive radiation, as is clear from its significantly higher emission, in particular in the wavelength region of 400-475 nm, i.e. about the maximum of the melatonin suppression sensitivity. Both lamps A and B have excellent color rendering indexes CRI>=80 and an efficacy of over 220 lumen/watt. In particular the lamp B is appropriate in the case that visual conditions are demanding and sleep quality should not be decreased. Applications can be found for people who wake up shortly in night hours or need to be inspected during night hours, for example at home for elderly but also for parents with young kids, elderly homes, hospitals, nursing homes.

The invention claimed is:
1. A method for controlling the alertness of a human subject via suitable light radiation, the human subject having a cycle of melatonin variation involving at least phases of a melatonin built-up and a melatonin degradation and being in a phase of said cycle, by suppressing or allowing said melatonin built-up or by stimulating said melatonin degradation, the method comprising the acts of;
  determining the phase of said cycle of melatonin variation in said human subject;

estimating a desired effect on the phase of said cycle of said human subject;

determining said suitable light radiation in dependence of said desired effect on the phase of said cycle as a function of spectrum, intensity, exposure period and interval period for one of suppressing melatonin built-up, allowing melatonin built-up, stimulating melatonin degradation and illumination of said human subject without substantially influencing the phase of said cycle;

selecting a light source having a light radiation output in accordance with said determined suitable light radiation output;

exposing an ocular region of the human subject during an exposure period to the suitable light radiation in dependence of said desired effect on the phase of said cycle, wherein the suitable light radiation is specified by an output fraction of melatonin suppressive radiation (Melatonin Watt/Watt) and light output (lumen/Watt), the output fraction and light output being adjusted to obtain the desired effect on the phase of said cycle.

2. A method as claimed in claim 1, characterized in that the output fraction of melatonin suppressive radiation is >=0.45 Melatonin Watt/Watt and the light output is <=60 lumen/watt.

3. A method as claimed in claim 1, characterized in that the output fraction of melatonin suppressive radiation is >=0.45 Melatonin Watt/Watt and the light output is <=20 lumen/Watt.

4. A method as claimed in claim 1, characterized in that the output fraction of melatonin suppressive radiation is >=0.45 Melatonin Watt/Watt and the light output is <=10 lumen/Watt.

5. A method as claimed in claim 1, characterized in that the output fraction of melatonin suppressive radiation is >=0.45 Melatonin Watt/Watt and the light output is >=60 lumen/Watt.

6. A method as claimed in claim 1, characterized in that the output fraction of melatonin suppressive radiation is >=0.45 Melatonin Watt/Watt and the light output is >=100 lumen/Watt, the light source having a color rendering index (CRI) >=65.

7. A method as claimed in claim 1, characterized in that the output fraction of melatonin suppressive radiation is >=0.6 Melatonin Watt/Watt and the light output is >=100 lumen/Watt, the light source having a color rendering index (CRI) >=65 and a color temperature of >=6500 K.

8. A method as claimed in claim 1, characterized in that the output fraction of melatonin suppressive radiation is <=0.2 Melatonin Watt/Watt and the light output is >=100 lumen/Watt, the light source having a color rendering index Ra>=65.

9. A method as claimed in claim 1, characterized in that the output fraction of melatonin suppressive radiation is <=0.1 Melatonin Watt/Watt and the light output is >=100 lumen/Watt, the light source having a color rendering index Ra>=65.

10. A method as claimed in claim 1, characterized in that the output fraction of melatonin suppressive radiation shifts from >=0.45 Melatonin Watt/Watt to <=0.2 Melatonin Watt/Watt or vice versa and the light output is >=100 lumen/Watt, the light source having a color rendering index Ra>=65.

11. A method as claimed in claim 1 characterized in that means for adjusting the suitable light radiation to be received by the human subject are chosen from the group consisting of filtering means, a shiftable light source and a lighting system comprising an adjustable first and second light source.

* * * * *